(12) United States Patent
Ritland

(10) Patent No.: US 6,309,396 B1
(45) Date of Patent: Oct. 30, 2001

(54) TOOL FOR INSERTING AN INTRAMEDULLARY GUIDE WIRE

(76) Inventor: G. David Ritland, 1663 34th St., NW., Washington, DC (US) 20007

( * ) Notice: Subject to any disclaimer, the term of this patent is extended or adjusted under 35 U.S.C. 154(b) by 0 days.

(21) Appl. No.: 09/025,815

(22) Filed: Feb. 19, 1998

(51) Int. Cl.$^7$ ..................................................... A61B 17/17
(52) U.S. Cl. ................................................. 606/96; 606/80
(58) Field of Search .................................. 606/79, 80, 96, 606/97, 98, 104, 108

(56) References Cited

U.S. PATENT DOCUMENTS 3,439,671 * 4/1969 Kuntscher .
5,624,447 * 4/1997 Myers ...................................... 606/96

OTHER PUBLICATIONS

Self Guiding Femoral AWL, Orthopaedic Designs Inc., Undated.
Fracture Management, Surgical Technique, ZMS Intramedullary Fixation with the ZMS Recon Nail, pp. 1–25, Richard F. Kyle, M.D., Chairman, Undated.
The Uniflex Nailing System, Surgical Technique, pp. 1–17, Biomet. Inc., Undated.

* cited by examiner

*Primary Examiner*—David O. Reip
(74) *Attorney, Agent, or Firm*—Shoemaker and Mattare

(57) ABSTRACT

A tool for inserting an intramedullary guide wire comprises a curved metal guide tube having a through lumen and a sharp point at its distal end, a handle for manipulating the tube, and a sighting guide affixed to the tube. The curvature of the guide tube enables the surgeon to align a drilling tool passed through the lumen with the axis of the femoral canal. The sighting guide has a straight distal portion parallel to a line tangent to the lumen axis at the distal end, so that the surgeon can better judge the position and orientation of the tip of the tool within the patient.

11 Claims, 4 Drawing Sheets

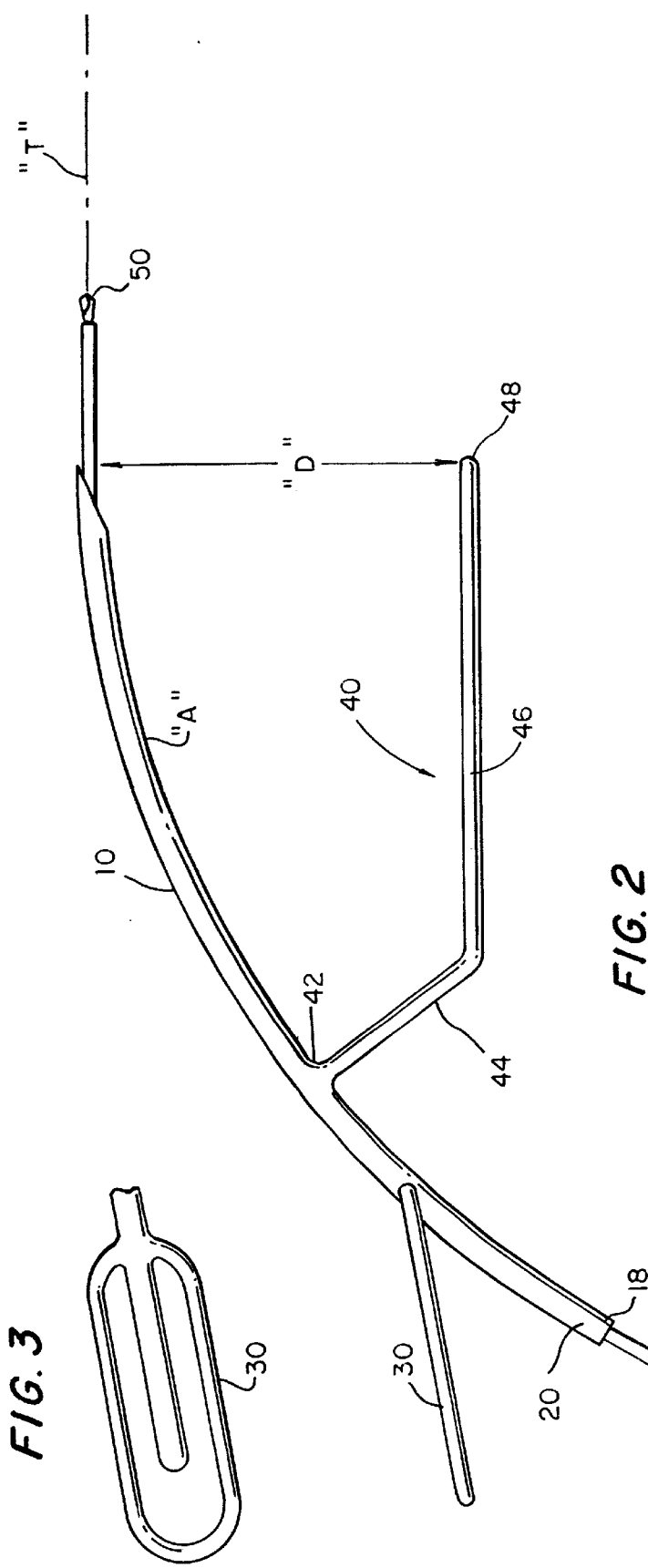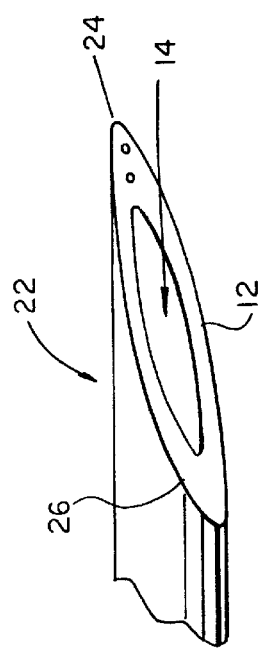

TOOL FOR INSERTING AN INTRAMEDULLARY GUIDE WIRE

BACKGROUND OF THE INVENTION

This invention relates to a tool for inserting an intramedullary guide wire.

Over the past twenty years, closed intramedullary rodding of the fractured femur has become a standard procedure. The procedure involves making a hole at the proximal end (top) of the femur, aligned with the femoral medullary canal, the inserting a guide wire through the hole into the canal, and then passing reamers down over the guide wire to enlarge the canal sufficiently that a long metal nail of sufficient diameter to reinforce and maintain alignment and orientation of the bone while it is healing may be inserted substantially the full length of the canal. Several difficult steps of this procedure have been simplified with new techniques and instrumentation, but accurate swift placement of the intramedullary guide wire is still a problem demanding time and tedious dissection.

Inserting a guide wire into the intramedullary canal of the femur would be much simpler if the surgeon could "see" along the axis of the canal. The leg is generally adducted (bent inward at the hip) to improve the situation, but the leg simply cannot be adducted enough so that the canal axis projects clear of the abductor muscle to allow straight insertion of a guide wire. In most cases, an attempt to insert a guide wire into the cancellous bone of the greater trochanter produces a deviated hole, and abrupt contact with the medial cortex, as shown in FIG. 1.

SUMMARY OF THE INVENTION

An object of the invention is to bend a guide wire so that its point can be drilled into the proximal femur while the remainder and the guide wire are positioned off to the side, away from the bulk of muscle and soft tissue between the greater trochanter and the iliac crest. This technique obviates the need to dissect the area of the piriformus fossa under direct vision. And there is no need to use an awl to open the femoral canal. Rather, the canal is opened by sliding an end-cutting reamer directly down the guide wire to the cortex and then turning the reamer. The present invention is intended to reduce the time required for guide wire placement, reduce bloody dissection near the bone, and thus reduce postoperative morbidity.

These and other objects are met by a tool for inserting an intramedullary guide wire, the tool having a curved metal guide tube with a through lumen and a sharp pointed bevel at its distal end, a handle for manipulating the tube, and a sighting guide affixed to the tube. The curvature of the guide tube enables the surgeon to align a drilling tool passed through the lumen with the axis of the femoral canal. The sighting guide has a straight distal portion parallel to a line tangent to the lumen axis at the distal end, so that the surgeon can better judge the position and orientation of the tip of the tool within the patient.

BRIEF DESCRIPTION OF THE DRAWINGS

In the accompanying drawings,

FIG. 2 is a plan view of a tool embodying the invention;

FIG. 3 is a rear elevation of a handle portion of the tool;

FIG. 4 is a detail at an enlarged scale of the tip of the tool;

DESCRIPTION OF THE PREFERRED EMBODIMENT

Figure 1:
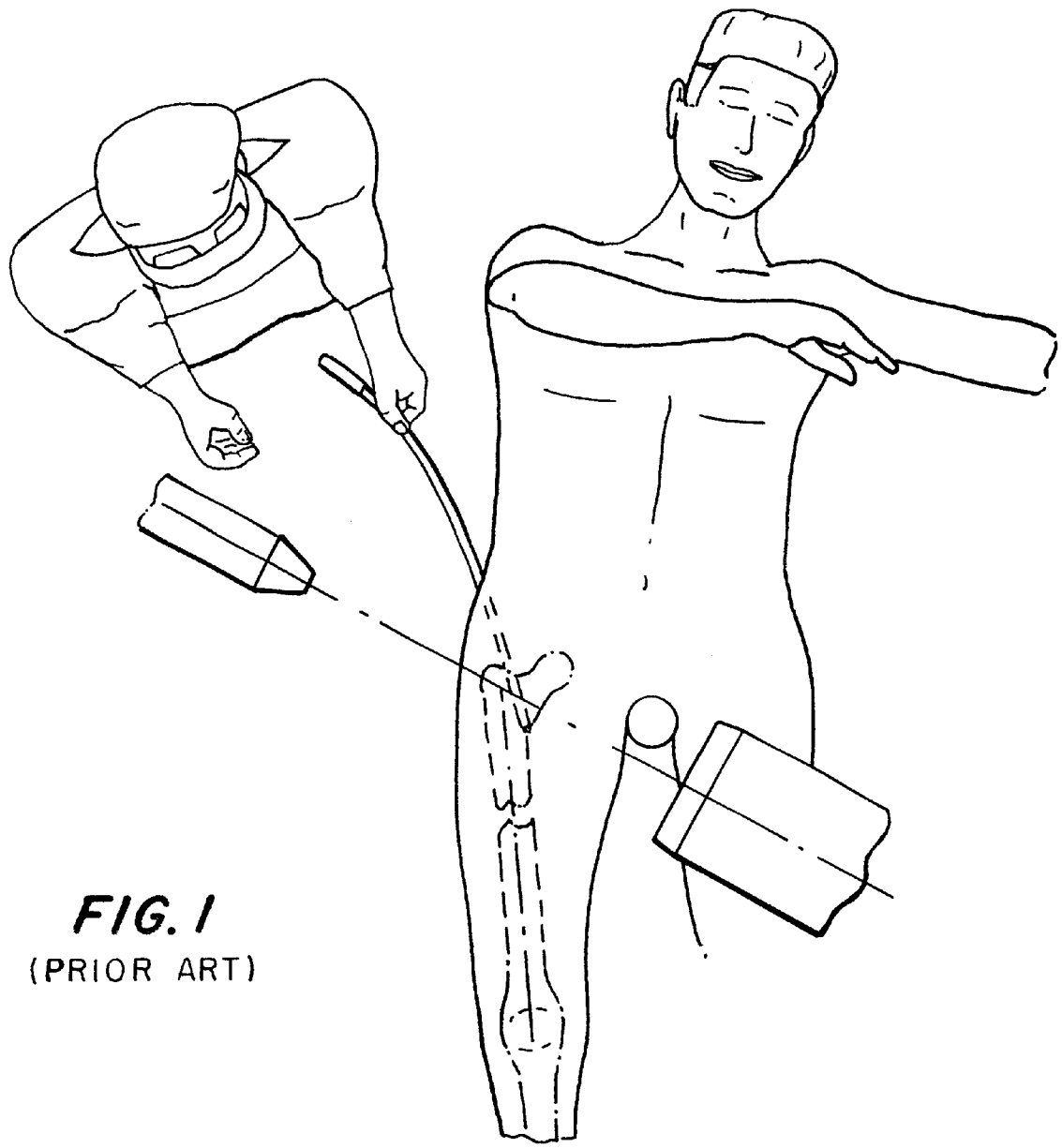
FIG. 1 is a plan view illustrating a current method of placing an intramedullary guide wire.
Figure 5:
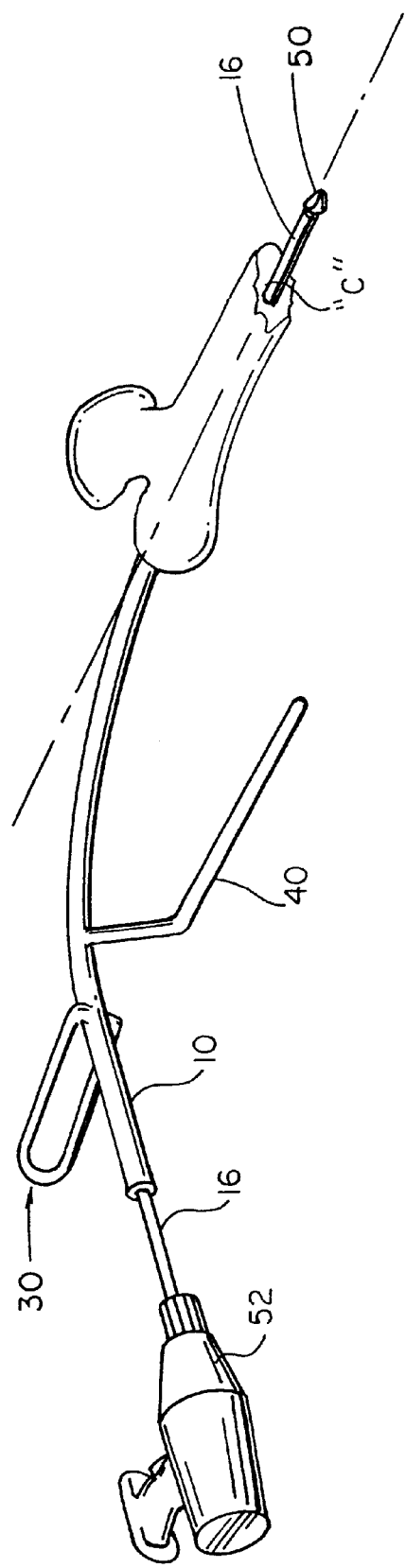
FIG. 5 is a perspective view showing the tool as utilized in a rod-placing procedure.
Figure 6:
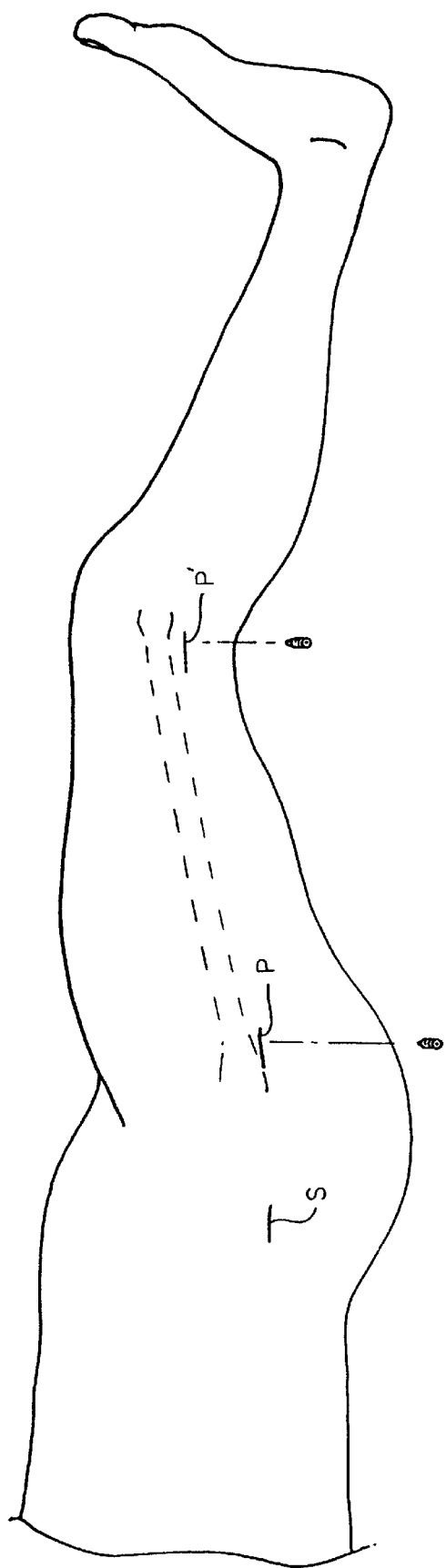
FIG. 6 is a perspective view showing the body surface and incisions made during the procedure.

A tool embodying the invention comprises a heavy-walled stainless steel guide tube 10 having a round through bore 12 of constant diameter forming a lumen 14 for the passage of a guide wire 16. The tube is bent, preferably, in a simple curve (i.e., in a single plane) at a constant radius, in the range often to sixteen inches. The proximal end 18 of the tube is square to the tube axis, and is countersunk at 20 to facilitate insertion of the guide wire. The distal end 22 of the tube is beveled at an acute angle, about 20°, so that it produces blunt dissection as it is pushed through muscle tissue. The foremost point 24 of the tip is sharp, but the remaining edges 26 of the tip are rounded slightly to avoid injuring tissue.

A handle 30 formed of an loop of stainless steel rod stock is welded to the guide tube, near the tube's proximal end 18. In an operation on the right leg of a patient, as illustrated, the handle would be grasped with the left hand. The position of the handle keeps the surgeons' hand well away from the X-ray beam used to observe progress of the tool.

A sighting guide 40 is affixed to the guide tube 10, at an intermediate point 42 distal to the handle. The sighting guide has a proximal portion 44, welded at its near end to the guide tube, and a distal portion 46 terminating at a rounded tip 48. The distal portion is straight, and parallel to a line "T" tangent to the lumen axis "A" at the distal end of the guide tube, so that the surgeon can better judge the position and orientation of the tip of the tool within the patient. I prefer that the perpendicular distance "D" from the sighting guide to the tube tip be about six inches.

In operation, an small incision is made through the skin and tensor fascia, and the tip of the guide tube is inserted, then pushed toward the greater trochanter while the surgeon observes its progress with an X-ray viewer. When the tip strikes the bone, the surgeon determines whether the axis of the bore coincides with that of the canal; if not, it may be possible to find the right spot by maintaining the tip against the bone and turning the tool, or it may be necessary to reposition the point on the femur. Once the tool has been properly positioned, the guide wire 16, which has a drill tip 50, is inserted through the guide tube until it contacts the cortex. Now, a drill motor 52 at the proximal end of the guide wire is activated, and a hole is drilled through the bone into the upper end of the femoral canal "C". The guide wire may now be pushed down into the canal, and the tool is withdraw over it, taking care not to drag the guide wire out of the canal.

With the guide wire in place, one can now pass a hollow reamer (not shown) over the guide wire and into the canal. Once the tip of the reamer is within the canal, it is rotated to produce a hole of uniform size correct for the intended femoral nail. This portion of the procedure is well known.

EXAMPLE

A muscular forty-year old construction worker in good health was struck by a motorcycle, and suffered a closed spiral fracture of the right femur. A closed intramedullary rodding of the femur was done the same day. Despite the patient's musculature, the incision required was only four centimeters long. It took less than ten minutes to make the incision, insert and position the guide tool, and drill the guide wire down to the proximal femur fragment. An initial incision was made with a scalpel through the skin and tensor fascia, the muscles below were blunt dissected by the tip of the guide tube, down to the head of the femur. After a femoral nail was inserted into the canal, puncture incisions were made to install proximal and distal locking screws through the nail. Postoperatively, there was no bleeding from the incision and the patient noticed pain at the fracture site, but not at the operative sites.

Since the invention is subject to modifications and variations, it is intended that the foregoing description and the accompanying drawings shall be interpreted as only illustrative of the invention defined by the following claims.

I claim:

1. A tool for forming a hole in the greater trochanter, aligned with the femoral medullary canal, said tool comprising:
   a curved metal guide tube having a constant radius of curvature, a through lumen and a sharp point at its distal end; and
   a handle for manipulating the tube,
      whereby the point of the tool can be positioned against the greater trochanter and aligned with the axis of the femoral canal without extreme adduction of the leg whereupon a guide wire having a drilling point may be passed through the guide tube and rotated from the proximal end of the tube to form said hole.

2. The invention of claim 1, wherein said radius of curvature is in the range of ten to sixteen inches.

3. The invention of claim 1, wherein the handle is connected to the tube near the proximal end of the tube.

4. The invention of claim 1, wherein the handle is a metal loop welded to the tube.

5. The invention of claim 1, wherein the lumen has an axis and the distal end of the tube is beveled on a plane making an acute angle with a line tangent to the axis of the lumen at said distal end.

6. The invention of claim 5, wherein said acute angle is about 20°.

7. The invention of claim 1, wherein said lumen is round in cross-section and of constant diameter.

8. A tool for forming a hole in the greater trochanter, aligned with the femoral medullary canal, said tool comprising
   a curved metal guide tube having a through lumen and a sharp point at its distal end, and
   a handle for manipulating the tube,
      whereby the point of the tool can be positioned against the greater trochanter and aligned with the axis of the femoral canal without extreme adduction of the leg whereupon a guide wire having a drilling point may be passed through the guide tube and rotated from the proximal end of the tube to form said hole,
      wherein the lumen has an axis, and further comprising a sighting guide affixed to the tube, the sighting guide having a straight distal portion parallel to a line tangent to the lumen axis at the distal end of the guide tube.

9. The invention of claim 8, wherein the sighting guide has a proximal portion substantially perpendicular to the tube at its junction therewith.

10. The invention of claim 9, wherein said junction is intermediate said ends of the guide tube.

11. The invention of claim 8, wherein a line perpendicular to the sighting guide, and extending perpendicularly therefrom, intersects the distal end of the guide tube.

* * * * *